United States Patent [19]
Partyka et al.

[11] 3,988,340
[45] Oct. 26, 1976

[54] 6-ALKOXYMETHYL-1,2,3,5-TETRAHYDROIMIDAZO[2,1-B]QUINAZOLIN-2-ONES AND 7-ALKOXYMETHYL-6-[H]-1,2,3,4-TETRAHYDROPYRIMIDO[2,1-B]QUINAZOLIN-2-ONES

[75] Inventors: Richard Anthony Partyka, Liverpool; Warren Neil Beverung, Jr., Minoa, both of N.Y.

[73] Assignee: Bristol-Myers Company, New York, N.Y.

[22] Filed: Jan. 23, 1975

[21] Appl. No.: 543,386

[52] U.S. Cl. .......................... 260/256.4 F; 424/251
[51] Int. Cl.² ...................................... C07D 487/04
[58] Field of Search ............... 260/256.4 F, 256.5 R

[56] References Cited
OTHER PUBLICATIONS

Beverung, et al., "Chemical Abstracts," vol. 79, (1973), Col. 115614b.

*Primary Examiner*—Nicholas S. Rizzo
*Assistant Examiner*—James H. Turnipseed
*Attorney, Agent, or Firm*—R. E. Havranek

[57] ABSTRACT

Optionally substituted 6-alkoxymethyl-1,2,3,5-tetrahydroimidazo[2,1-b]-quinazolin-2-ones and 7-alkoxymethyl-6-[H]-1,2,3,4-tetrahydropyrimido[2,1-b]-quinazolin-2-ones or the pharmaceutically acceptable salts thereof are compounds useful as blood platelet anti-aggregative and/or antihypertensive and/or bronchodilator agents in mammals, including humans.

14 Claims, No Drawings

6-ALKOXYMETHYL-1,2,3,5-TETRAHYDROIMIDAZO[2,1-B]QUINAZOLIN-2-ONES AND 7-ALKOXYMETHYL-6-[H]-1,2,3,4-TETRAHYDROPYRIMIDO[2,1-B]QUINAZOLIN-2-ONES

BACKGROUND OF THE INVENTION

1. Field of the Invention

The compounds of the present invention are useful in the control of mild to severe hypertension, as anti-clotting agents and bronchodilators.

2. Description of the Prior Art

The compounds of the present invention are new and novel. The literature discloses the following prior art:

A. The compounds characterized as 1— and 9-alkyl-2,3-dihydroimidazo-[1,2—a]-benzimidazoles [R. J. North and A. R. Day, J. Hetero, Chem., 655 (1969)]. The compounds have the following structure:

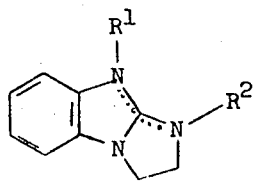

in which $R^1$ and $R^2$ are optionally substituted with alkyl functions.

B. B. Loev, T. Jen and R. A. McLean, Experientia, 27, 875 (1971) disclose the compound having the formula

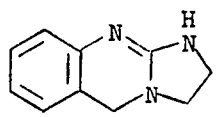

as having potent antihypertensive activity in rats, dogs, cats and rabbits.

C. R. Grout and M. Partridge, J. Chem. Soc., 3551 (1960) report the synthesis of the compound

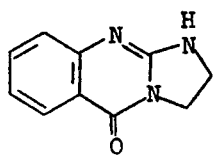

No antihypertensive activity was reported.

D. K. Lempert and G. Doleschall, Experientia, 18, 401 (1962) and Acta Chimica Academiae Scientiarum Hungaricae, 45, 357–68 (1965) report the synthesis of the compounds

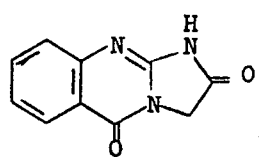

No antihypertensive activity was reported.

E. A. Simonov et al., Khim. Farmatseut. Zh., (1969) [Annual Reports in Medicinal Chemistry, Chapt. 6, 53 (1969) ] report the preparation of 9-substituted imidazobenzimidazoles having the formula

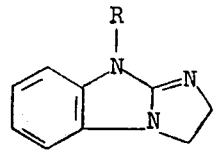

said compounds reported to have hypotensive effects in animals but no detailed data was presented.

F. G. E. Hardtmann, German Pat. No. 2,025,248 (1970) reports bronchodilating and hypotensive effects for the compounds having the formula

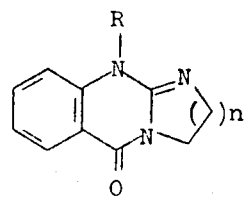

G. T. Jen et al., J. Med. Chem., 15 (7), 727–31 (1972) describe the compounds having the formula

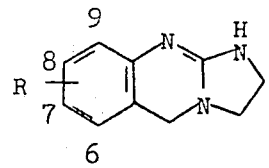

in which R is H, 6-Cl, 7-Cl, 7-MeO, 7-OH, 8-Cl, 9-Cl and 9-$CH_3$ as being hypotensive agents.

H. Beverung et al, Belgian Pat. No. 794,964 describe the compounds having the formula

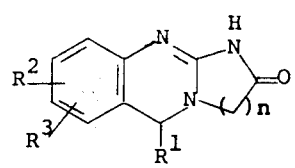

in which $R^1$ is H, phenyl or (lower)alkyl, $R^2$ and $R^3$ are alike or different and are hydrogen, chloro, bromo, fluoro, (lower)alkyl, hydroxy, nitro, amino, (lower)alkoxy or phenyl, or when taken together $R^2$ and $R^3$ are methylenedioxy, and n is an integer of 1 or 2; or a pharmaceutically acceptable acid addition salt thereof as hypotensive and/or blood platelet anti-aggregative agents.

SUMMARY OF THE INVENTION

The compounds having the formula

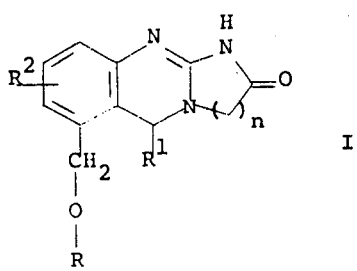

in which $R^1$ is H, phenyl or (lower)alkyl, R is (lower)alkyl, $R^2$ is hydrogen, chloro, bromo, fluoro, $CF_3$, hydroxy, nitro, amino or (lower)alkyl of 1 to 3 carbon atoms or (lower)alkoxy of 1 to 3 carbon atoms, and n is an integer of 1 or 2; or a pharmaceutically acceptable acid addition salt thereof are hypotensive, blood platelet antiaggregative and/or bronchodilator agents.

DETAILED DESCRIPTION

This invention relates to new synthetic compounds of value as hypotensive and blood platelet antiaggregative agents. Most particularly the compounds of the invention are 6-(lower)alkoxymethyl-1,2,3,5-tetrahydroimidazo[2,1-b]-quinazolin-2-ones having the formula

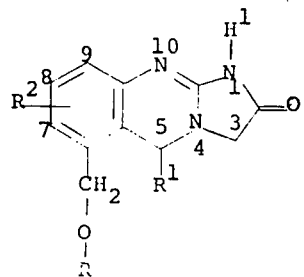

or 7-(lower)alkoxymethyl-6-[H]-1,2,3,4-tetrahydropyrimido-[2,1-b]quinazolin-2-ones having the formula

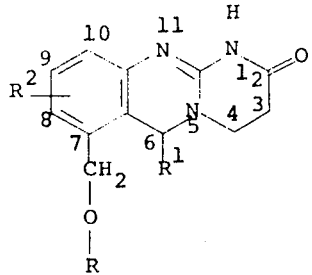

in which $R^1$ is H, phenyl or (lower)alkyl, R is (lower)alkyl, $R^2$ is hydrogen, chloro, bromo, fluoro, $CF_3$, (lower)alkyl of 1 to 3 carbon atoms, hydroxy, nitro, amino or (lower)alkoxy of 1 to 3 carbon atoms, or a pharmaceutically acceptable acid addition salt thereof.

Hypertension is a rather common and serious disease, particularly in elderly people. High blood pressure, a result of hypertension, is a common but serious disease. Most particularly, hypertension is often the cause of crippling or fatal strokes in the elderly. It was therefore an object of the present invention to provide compounds useful in the treatment of mild to severe hypertension.

Subsequent to the preparation of some of the compounds of the present invention, it was found that most of the compounds also possessed unique properties as blood platelet anti-aggregative agents. These compounds are useful in the prevention of intravascular thrombosis, prevention of coronary thrombosis, prevention of transient ischemic episodes, prevention of platelet thrombosis in the use of prosthetic devices (artificial heart valves, etc.). A large number of the compounds of the present invention have also been found to possess desirable bronchodilator activity in mammals.

The objects of the present invention have been achieved by the provision of the compound having the formula

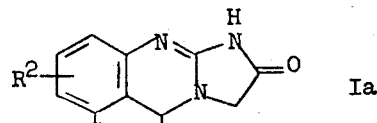

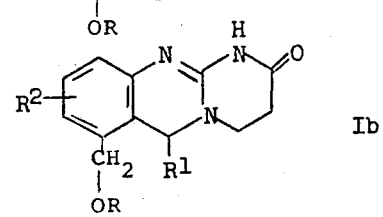

in which $R^1$, $R^2$ and R are as defined above.

For the purpose of this disclosure, the compounds of the present invention are represented as having the formulas Ia and Ib. However, compounds Ia and Ib can exist in several possible tautomeric forms, e.g.:

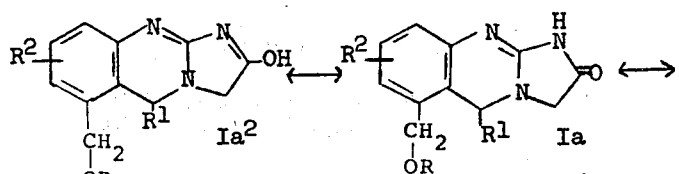

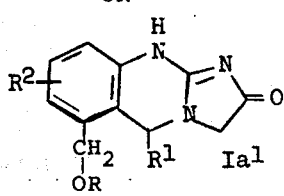

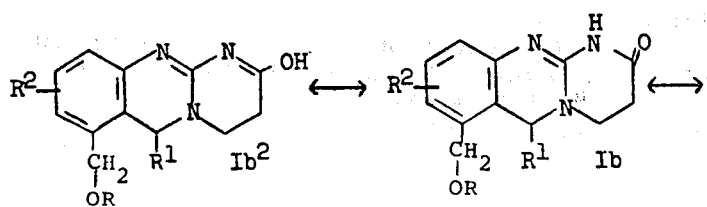

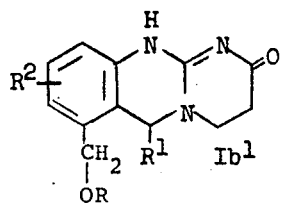

All the possible tautomers are considered an integral part of the present invention and all these forms are considered included when the compounds are represented as formula Ia or Ib.

Also considered as integral part of this invention are the optical isomers of those compounds having an asymetric center, e.g., (+) and (−)-6-methoxymethyl-5-methyl-1,2,3,5-tetrahydroimidazo[2,1-b]-quinazolin-2-one. The racemic mixture of these compounds are resolved by those methods commonly known in the art.

The nontoxic salts that are pharmaceutically acceptable include the hydrochlorides, hydrobromides, hydroiodides, (lower)alkylsulfates, (lower)alkyl and aryl sulfonates, phosphates, sulfates, maleates, fumarates, succinates, tartrates, citrates, and other commonly used in the art.

The salts obtained through the variation of the acid used in some cases have special advantage due to increased stability, increased solubility, decreased solubility, ease of crystallization, lack of objectionable taste, etc., but these are all subsidiary to the main physiological action of the free base, which is independent of the character of the acid used in the preparation of the salt.

Most of the compounds of the present invention can be prepared as shown in Chart I.

Chart I

Step 1

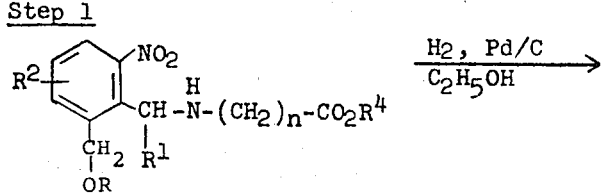

III

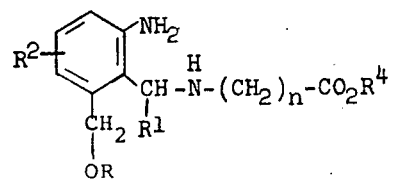

IV

Step 2

IV  $\xrightarrow{\text{BrCN}}$  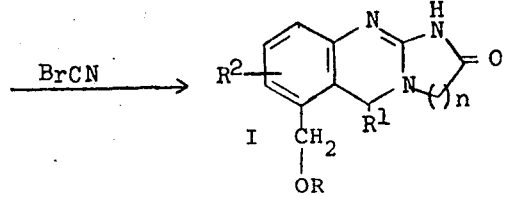

I $R^1$, $R^2$ and R and n are as defined above and $R^4$ is (lower)alkyl.

In other cases, particularly when $R^2$ is a bromine, chlorine, amino, or $NO_2$, it may be desirable to halogenate or nitrate after producing compound I (see examples).

Two alternative processes for the preparation of the compounds of the instant invention are found in Charts II and III. In some instances, these are the preferred synthetic route.

Chart II

Step 1:

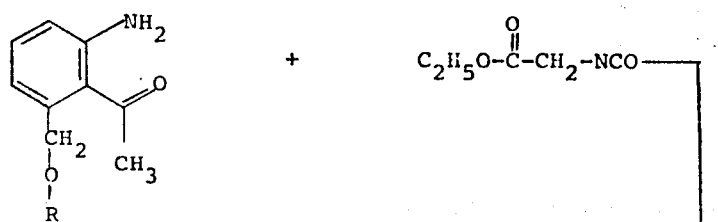

Step 2:

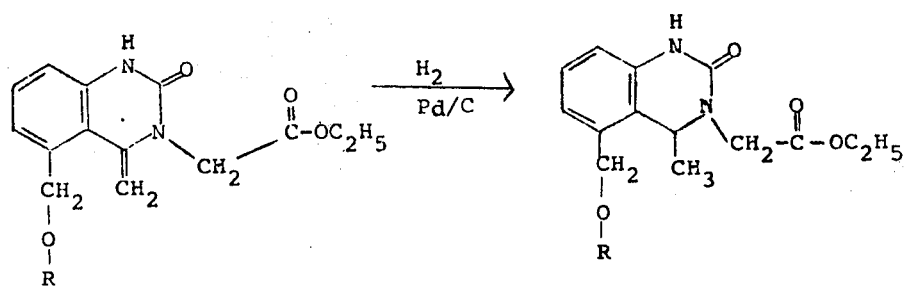

Step 3:

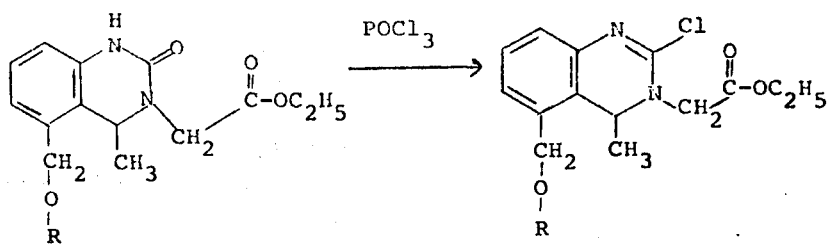

Step 4:
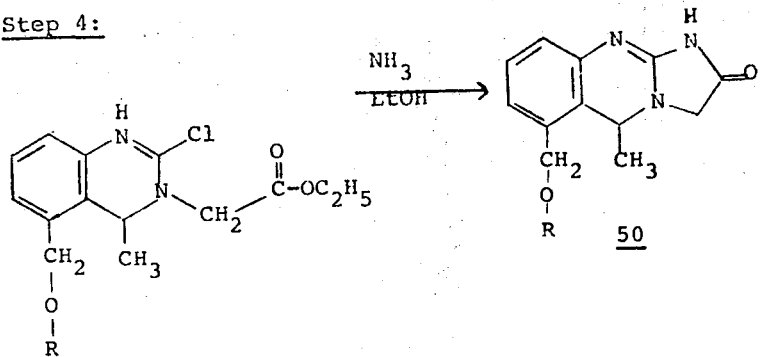
Chart III
Step 1:
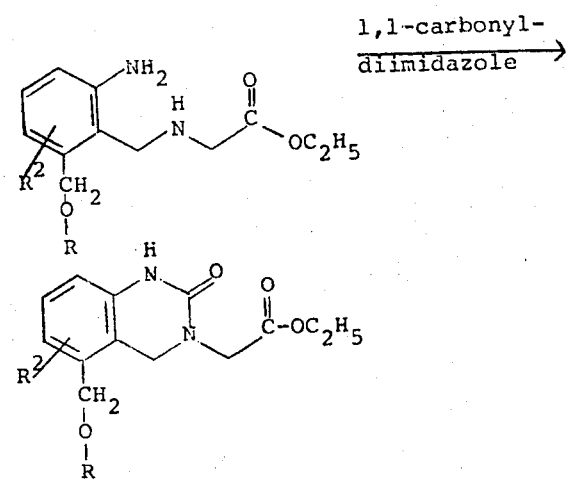
Step 2:
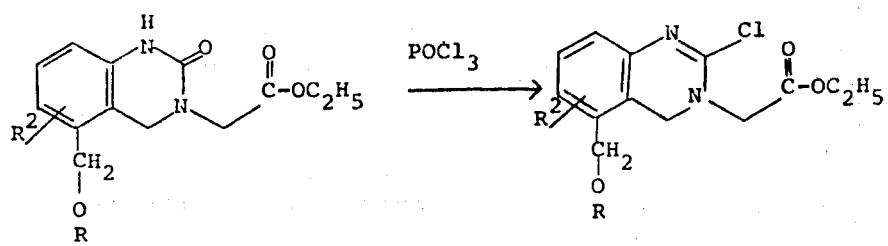
Step 3:
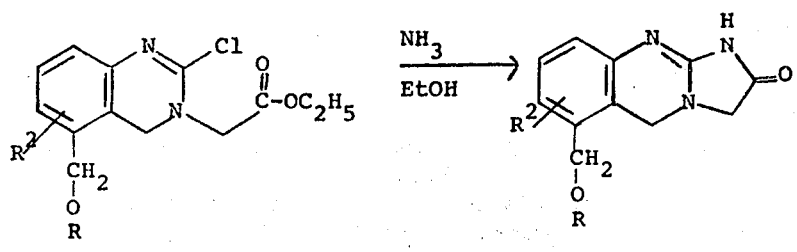

Compounds possessing a substituent at positions 5 and 6 are preferably prepared by the synthetic route illustrated by Chart II.

The objectives of the present invention have been achieved by the provision according to the present invention, of the process for the synthesis of compounds having the formula

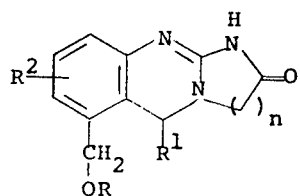

in which $R^1$ is H, phenyl or (lower)alkyl, R is (lower)alkyl, $R^2$ is hydrogen, chloro, bromo, fluoro, $CF_3$, hydroxy, nitro, amino or (lower)alkyl of 1 to 3 carbon atoms or (lower)alkoxy of 1 to 3 carbon atoms; and n is an integer of 1 or 2; which process is characterized by treating one mole of the compound having the formula

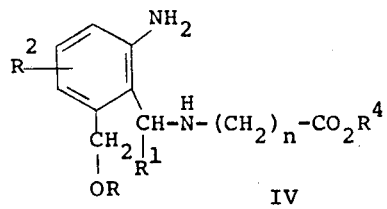

in which $R^1$, $R^2$, $R^3$ and $R^4$ are n are as defined above with at least one mole of cyanogen bromide to produce compound I.

A further preferred embodiment is the process for the preparation of compound I which process is characterized by treating compound IV with cyanogen bromide in a ratio of at least one mole of cyanogen bromide per mole of compound IV in a reaction inert solvent system with the aid of heat to produce compound I.

A still more preferred embodiment is the process for the preparation of the compound having the formula

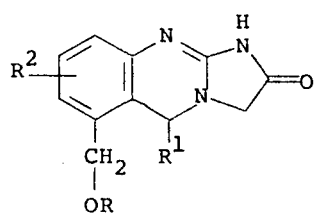

in which $R^1$ is H or (lower)alkyl, R is (lower)alkyl, $R^2$ is hydrogen, chloro, bromo, fluoro, $CF_3$, hydroxy, nitro, amino or (lower)alkyl of 1 to 3 carbon atoms or (lower)alkoxy of 1 to 3 carbon atoms; which process is characterized by treating the compound having the formula

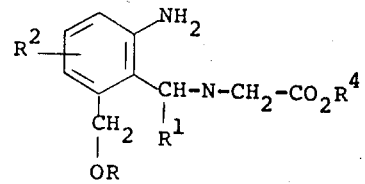

in which R, $R^1$, $R^2$ and $R^4$ are as defined above with cyanogen bromide, in a ratio of 1.0 to 1.2 moles of cyanogen bromide per mole of compound IV, in a reaction inert organic solvent selected from the group consisting of ethanol, n-propanol, isopropanol and methanol, with or without the presence of some water, at about reflux temperatures, to produce compound I.

The pharmaceutically acceptable, nontoxic salts of compound I are readily prepared by the addition of stoichiometric (or larger quantities) of the desired acid to a solution of compound I. Since compound I has only one strongly basic grouping, it only forms monosalts, e.g., monohydrochloride.

A preferred embodiment of the present invention is the compound having the formula

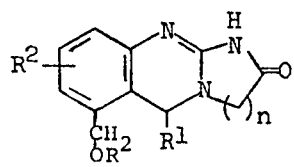

in which $R^1$ is H, phenyl or (lower)alkyl, R is (lower)alkyl, $R^2$ is hydrogen, chloro, bromo, fluoro, $CF_3$, hydroxy, amino, nitro, (lower)alkyl of 1 to 3 carbon atoms or (lower)alkoxy of 1 to 3 carbon atoms, and n is an integer of 1 or 2; or a pharmaceutically acceptable acid addition salt thereof.

A more preferred embodiment is the compound having the formula

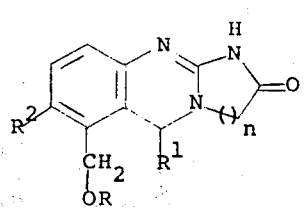

in which $R^1$ is H, phenyl or (lower)alkyl, R is (lower)alkyl, $R^2$ is hydrogen, chloro, bromo, fluoro, $CF_3$, (lower)alkyl of 1 to 3 carbon atoms or (lower)alkoxy of 1 to 3 carbon atoms, hydroxy, nitro or amino, and n is an integer of 1 or 2; or a pharmaceutically acceptable acid addition salt thereof.

A more preferred embodiment is the compound having the formula

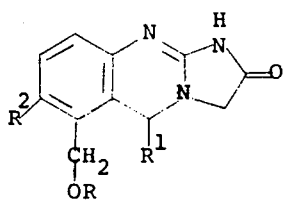

in which $R^1$ is H, phenyl or (lower)alkyl, R is (lower)alkyl, $R^2$ is hydrogen, chloro, bromo, fluoro, $CF_3$, hydroxy, (lower)alkyl of 1 to 3 carbon atoms, or (lower)alkoxy of 1 to 3 carbon atoms, nitro, amino, or a pharmaceutically acceptable acid addition salt thereof.

A still more preferred embodiment is the compound having the formula

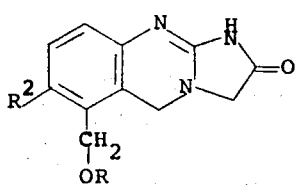

in which R is (lower)alkyl of 1 to 3 carbon atoms, $R^2$ is hydrogen, $CF_3$, chloro, bromo, fluoro, nitro, amino, hydroxy, (lower)alkoxy of 1 to 3 carbon atoms, methyl or a pharmaceutically acceptable acid addition salt thereof.

A most preferred embodiment is the compound having the formula

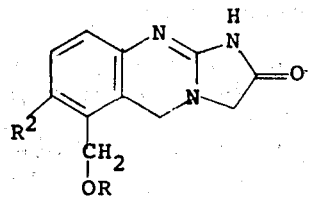

in which R is (lower)alkyl of 1 to 2 carbon atoms, $R^2$ is H, hydroxy, methyl, methoxy, chloro or fluoro; or a pharmaceutically acceptable salt thereof.

Another more preferred embodiment is the compound having the formula

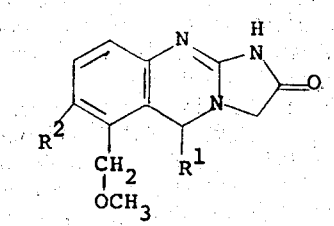

IM in which $R^2$ is H, Cl, methoxy, methyl, nitro or hydroxy, $R^1$ is H, phenyl or methyl; or the hydrochloride salt thereof.

The most preferred embodiments are the compounds of formula IM which are substituted as follows:
1. $R^1$ and $R^2$ are H; or the hydrochloride salt thereof.
2. $R^1$ is methyl and $R^2$ is H; or the hydrochloride salt thereof.
3. $R^2$ is chloro and $R^1$ is H; or the hydrochloride salt thereof.

For the purpose of this disclosure, the term (lower)alkyl shall mean straight and branched chain saturated aliphatic groups having 1 to 6 carbons inclusive unless otherwise stated. The term (lower)alkanol or (lower)alkoxy shall have the same connotation, an alcohol or alkoxy group of 1 to 6 carbons inclusive unless otherwise stated.

Pharmacological evaluation has indicated the compounds of the present invention possess hypotensive activity.

The blood pressure of unanesthetized rats and dogs was measured directly by means of a transducer attached to an intra-arterial cannula and in anesthetized dogs by a mercury manometer attached to a carotid cannula.

The compounds of the instant invention were tested as the hydrochloride salts by the above method in normotensive rats in doses of 50 mg./kg. orally.

At the present time, indications are that the compounds do not appear to be acting in the same way as 2-(2,6-dichloroanilino)-2-imidazoline hydrochloride ["CATAPRES"]. Their activity is probably not attributable to α-adrenergic blockade or to ganglionic blocking action.

In the treatment of hypertension in animals including man, the compounds of the present invention are administered orally and/or parenterally, in accordance with conventional procedures for the administration of hypotensive agents in an amount of from about 0.5 mg./kg./ does to 30 mg./kg./dose depending upon the route of administration and the particular compound of the invention. The preferred dosage for the compounds of the invention is in the range of about 1.0 to 15.0 mg./kg./ dose two to four times a day. Similar doses are used to obtain in vivo inhibition of platelet aggregation in animals, including man.

Compound 12a (BL-4784a) was tested for its hypotensive activity in rats as follows:

Rats were dosed orally with the test drug (50 mg/kg) or saline and blood pressure measurements were made at 30, 90, 150 and 300 mins. after drug administration.

RESULTS

As shown below, BL-4784 resulted in significant lowering of aortic blood pressure following oral administration of 50 mg/kg. Saline administration in a volume equivalent to drug administration had only a minimal effect.

| Compound | Time in Min | Mean Aortic Blood Pressure mm Hg | % Change |
|---|---|---|---|
| BL-4784 (N=9) [structure: benzene ring with N=C-N-C(=O) imidazolinone substituent and CH₂-O-CH₃ group] | 0 | 111 ± 3 | — |
| | 30 | 73 ± 5* | −33 ± 4 |
| | 90 | 79 ± 3* | −27 ± 4 |
| | 150 | 84 ± 3* | −23 ± 2 |
| | 300 | 87 ± 3* | −20 ± 4 |
| Saline (N=2) | 0 | 110 ± 10 | — |
| | 30 | 105 ± 10 | −4 ± 0.5 |
| | 90 | 105 ± 6 | −4 ± 4 |
| | 150 | 105 ± 2 | −4 ± 2 |
| | 300 | 100 ± 5 | −8 ± 4 |

Values are mean ± 1 S. E.
N = Number of experiments.
*P = <.05. P refers to comparison of the difference between control values before the drug and values for the drug response by means of the t-test for unpaired data.

References

Buyniski, J. P. Cavanagh, R. L. and Bierwagen, M. E. Reduction of tissue norepinephrine and aortic pressure in spontaneously hypertensive rats by 1,2,3,5-tetrahydroimidazo[2,1-b]quinazoline. Res. Communic. Chem. Pathol. & Pharmacol. 5:647–653, 1973.

Pharmacological evaluation has also indicated the compounds of the present invention possess blood platelet anti-aggregative activity.

The aggregometer method of Born (1), as modified by Mustard et al. (2) was used to assess the in vitro activity of the various compounds as to inhibition of adenosine diphosphate (ADP) and collagen induced platelet aggregation. Platelet rich plasma was separated by centrifugation from citrated (3.8 percent) rabbit blood. ADP in final concentration of 0.5 mcg./ml. or 0.05 ml. of a collagen suspension prepared according to the method described by Evans et al. (3) was used to induce aggregation. The various compounds tested were dissolved in dimethylsulfoxide (DMSO) so that 5 mcl. added to the platelet rich plasma would yield the desired test concentration. Vehicle control trials were done and compared with aggregation induced in platelet rich plasma containing various concentrations of the test compounds. Dose response curves were obtained and Effective Concentration (EC50) values calculated.

Compound 12a (BL-4784A) has been evaluated in a series of in vitro, ex vivo and in vivo animal models of platelet aggregation and thrombosis. In vitro, the compound was evaluated in the aggregometer for its ability to inhibit platelet aggregation induced by adenosine diphosphate (ADP), 2.93 × 10⁻⁵M; collagen, according to the method of Evans et al. (3); thrombin, 1 unit per ml; antigen-antibody complexes (egg albumin) 2 μg/ml added to platelet rich plasma (PRP) obtained from sensitized rabbits, and arachidonic acid, 50 μg/ml.

A summary of these in vitro results is presented in the table below.

| System | BL-4784A EC50 & 95% Confidence Limits (μg/ml) |
|---|---|
| Rabbit Platelet Rich Plasma | |
| ADP | 0.20 (0.14–0.28) |
| Collagen | 0.09 (0.07–0.11) |
| Thrombin | 0.63 (0.44–0.89) |
| Antigen-Antibody complex | 0.13 (0.10–0.16) |
| Arachidonic acid | 0.27 (0.17–0.39) |
| Dog Platelet Rich Plasma | |
| ADP | 0.19 (0.15–0.25) |

BL-4784A was also tested ex vivo in dogs where ADP was used to induce aggregation in PRP samples obtained before and 1 hr. after oral drug administration. In this model, BL-4784A had an ED50 of 1.79 (1.17–2.93) mg/kg.

BL-4784A has also shown significant activity in three in vivo animal models; biolaser induced thrombosis in the rabbit ear chamber, ED50 = 5.3 mg/kg po; electrically induced carotid artery thrombosis in the dog, ED50 = 10.5 mg/kg po. Methodology for these three in vivo techniques has been previously reported (4, 5).

References:
1. Born, G.V.R. J. Physiol., London, 162, 67P (1962).
2. Mustard, J. F., Hegardt, B. Rowsell, H. C. and MacMillan, R. L., J. Lab. Clin. Med. 64, 548 (1964).
3. Evans, G. Marian, M. C., Packham, M. A., Nishizawa, E. E., Mustard, J. F. and Murphy, E. A., J. Exp. Med., 128, 877 (1968).
4. Herrmann, R. G. and Lacefield, W. B. Effect of Antithrombotic Drugs on In vivo Experimental Thrombosis. In Platelets and Thrombosis, pp. 203–221, Ed. S. Sherry and A. Scriabine, University Park Press, Baltimore.
5. Fleming, J. S., Buchanan, J.O., King, S.P., Cornish, B. T. and Bierwagen, M. E. Use of the Biolaser in the Evaluation of Antithrombotic Agents. In Platelets and Thrombosis, pp. 247–262, Ed. S. Sherry and A. Scriabine, University Park Press, Baltimore.

Before dosing the animals, blood samples are taken. The blood is centrifuged to obtain the blood platelet-rich plasma. Aggregation of this plasma is induced with ADP or collagen. This is the control.

The animals are then dosed with the compounds to be tested (orally or parenterally). Depending upon the route of administration, one to two hours are allowed to elapse after dosing. Blood is drawn and the same procedure as for the control in untreated animals.

The dose required to produce 50% inhibition of the aggregation is determined by dose response data obtained in this manner.

Compound 12a of this invention is superior in many respects to the blood platelet antiaggregative compounds found in Belgain Pat. No. 794,964, which patent has issued to these same inventors.

The most promising blood platelet antiaggregative compound of that patent was the compound having the following formula

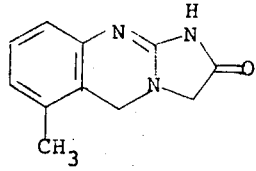

BL-3459a

Unfortunately, upon extensive pharmacological examination, BL-3459 or a metabolite thereof formed crystals in the liver of dogs at very high doses. Compound 12a does not appear to possess that liability in that it or its metabolite is more soluble in vivo and no crystal deposits have been observed in any tissue of any animal species in which it has been evaluated up to the present time. In addition, compound 12a is more potent than BL-3459 as a blood platelet antiaggregate and has a lower degree of hypotensive activity associated with this activity. This is desirable in that it possesses fewer side effects and is more specific in its activity.

EXPERIMENTAL

All products described are supported by satisfactory infrared (IR) and nuclear magnetic resonance (nmr) spectra. Melting points are uncorrected. Temperatures are expressed in degrees Centigrade (°C.) and pressure in millimeters of mercury (mm).

EXAMPLE 1

Preparation of 2-(α-bromomethyl)-6-nitrobenzoic acid methyl ester (5a).

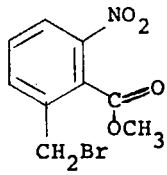

To a solution of 50.0 g (0.254 mole) of (2-methyl-6-nitro) methyl benzoate in 2.5 l of carbon tetrachloride was added 55.0 g (0.308 mole) of N-bromosuccinimide and 1.0 g of benzoyl peroxide. The mixture was heated to reflux for 16 hrs., cooled and filtered. The solvent was removed in vacuo and the residue cyrstallized from hexane (1.5 l) affording 43.0 g (62% yield) of a colorless solid which is strong lachrymator and skin irritant. The solid was identified as the title product.

EXAMPLE 2

Preparation of 2-(α-methoxymethyl)-6-nitrobenzoic acid methyl ester (6a).

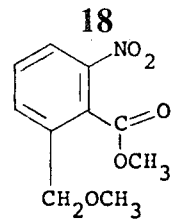

To a refluxing solution of 43.4 g (0.157 mole) of 2-(α-bromomethyl)-6-nitrobenzoic acid methyl ester (5a) in 600 ml of methanol was added dropwise a solution of freshly prepared sodium methoxide (0.314 mole) in 400 ml of methanol. Upon complete addition, the solution was refluxed for 1 hr., cooled to room temperature and water (250 ml) added. The methanol was removed in vacuo, the insoluble oil extracted into ether (250 ml.), and the aqueous solution extracted with ether (2×250 ml). The etheral extracts were combined, washed with water, dried (Na$_2$SO$_4$) and the solvent removed in vacuo affording 27.8 g (85%) of an orange oil. Purification was effected by distillation yielding a yellow oil; bp 111°–112° C. (0.05 mm).

Anal. Calc'd. for C$_{10}$H$_{11}$NO$_5$: C, 53.33; H, 4.93; N, 6.22. Found: C, 53.29; H, 4.81; N, 6.19.

EXAMPLE 3

Preparation of 2-(α-methoxymethyl)-6-nitrobenzoic acid (7a).

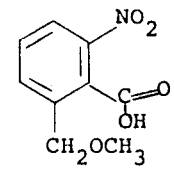

To a solution of 25.5 g (0.113 mole) of 2-(α-methoxymethyl)-6-nitrobenzoic acid methyl ester (6a) in 50 ml of methanol was added 175 ml of 1M NaOH (0.175 mole) and the mixture refluxed for 2.5 hrs. The solution was cooled to room temperature, the methanol removed in vacuo, and the aqueous solution made acidic by the slow addition of 3N hydrochloric acid. The insoluble material was extracted into methylene chloride, the acidic aqueous solution extracted with methylene chloride, the extracts combined and washed with a saturated sodium chloride solution. The methylene chloride extract was dried (Na$_2$SO$_4$) and the solvent removed in vacuo yielding 24.1 g of a yellow oil. Purification was affected by crystallization from carbon tetrachloride yielding 18.8 g (79% yield) of a colorless solid: mp 63°–4°.

EXAMPLE 4

Preparation of 2-(α-methoxymethyl)-6-nitrobenzyl alcohol (8a).

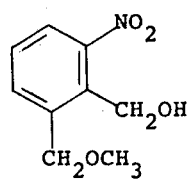

To a solution of 10.9 g (52 mmole) of 2-(α-methoxymethyl)-6-nitrobenzoic acid (7a) in 175 ml of tetrahydrofuran was added 65 ml (65 mmole) of a stock 1M borane/tetrahydrofuran solution and the solution heated to reflux for 18 hrs. The solution was cooled in an ice bath, the reaction quenched by the dropwise addition of 10% hydrochloric acid (65 ml) and the mixture heated to reflux for 1 hr. The tetrahydrofuran was distilled at atmospheric pressure, the solution cooled and water (100 ml) added. The insoluble oil was extracted into methylene chloride, washed with saturated sodium bicarbonate solution, dried ($Na_2SO_4$) and the solvent removed in vacuo yielding 10.3 g of a colorless solid. Purification was effected by crystallization from methyl cyclohexane/n-pentane affording 9.14 g (89% yield) of a colorless solid; mp 69°–70°.

Anal. calc'd. for $C_9H_{11}NO_4$: C, 54.82; H, 5.62; N, 7.21. Found: C, 54.82; H, 5.77; N, 7.21

EXAMPLE 5

Preparation of 2-(α-methoxymethyl)-6-nitrobenzyl chloride (9a).

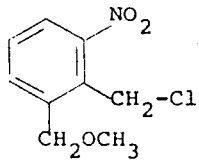

To a mixture of 11.8 g (60 mmole) of 2-(α-methoxymethyl)-6-nitrobenzyl alcohol (8a) and 0.3 ml of pyridine in 125 ml of benzene was added a solution of 14.3 g (120 mmole) of thionyl chloride in 50 ml of benzene and the solution heated at reflux for 2 hrs. The solution was cooled to 0°, the reaction quenched by the slow addition of water (75 ml), the organic phase separated and washed with dilute sodium bicarbonate. The organic extract was dried ($Na_2SO_4$) and the solvent removed in vacuo affording 13.0 g (95% yield) of a brown oil identified as the title product. The sample was of sufficient purity to be used as such.

EXAMPLE 6

Preparation of N-[2-(α-methoxymethyl)-6-nitrobenzyl]-glycine ethyl ester (10a).

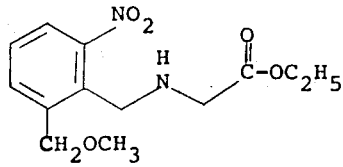

To a suspension of 33.4 g (0.24 mole) of glycine ethyl ester hydrochloride in 200 ml of absolute ethyl alcohol was added under a nitrogen atmosphere a solution of 30.6 g (0.30 mole) of triethylamine in 140 ml. of absolute ethyl alcohol. The mixture was heated to reflux and a solution of 13.0 g (0.06 mole) of 2-(α-methoxymethyl)-6-nitrobenzyl chloride (9a) in 140 ml of absolute ethyl alcohol was added over a 45 min. period. Upon complete addition, the mixture was allowed to reflux an additional 17 hrs., cooled to room temperature and the solvent removed in vacuo. To the solid residue was added 100 ml of water and enough 10% hydrochloric acid to make the solution acidic (pH~3). The acidic solution was washed with methylene chloride (2×50 ml), made neutral by the addition of 40% sodium hydroxide, and the insoluble oil extracted with ether. The etheral extract was washed with water, dried ($K_2CO_3$) and the solvent removed in vacuo affording 14.0 g (82% yield) of a colorless oil identified as the title product. Purification was effected by salt formation (HCl/ether): mp 154°–6°.

Anal. Calc'd. for $C_{13}H_{18}N_2O_5\cdot HCl$: C, 48.99; H, 6.01; N, 8.78. Found: C, 48.78; H, 5.87; N, 8.82.

EXAMPLE 7

Preparation of N-[2-(α-methoxymethyl)-6-aminobenzyl]glycine ethyl ester (11a).

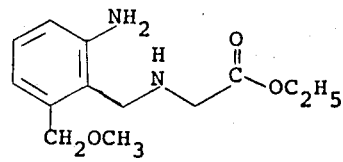

To a solution of 14.0 g (50 mmole) of N-[2-(α-methoxymethyl)-6-nitrobenzyl]glycine ethyl ester (10a) in 250 ml of absolute ethyl alcohol was added slowly 0.70 g of 5% Pd/C catalyst and the mixture placed on a Paar hydrogenator. The mixture was shaken until theoretical hydrogen (150 mmole) had been absorbed, removed from the Paar and the mixture filtered under suction. The catalyst was washed with ethyl alcohol and the solvent removed in vacuo affording 12.0 g (92% yield) of a clear yellow oil identified as the title product. The sample was of sufficient purity to be used as such.

EXAMPLE 8

Preparation of 6-(α-methoxymethyl)-1,2,3,5-tetrahydroimidazo[2,1-b]quinazolin-2-one (12a).

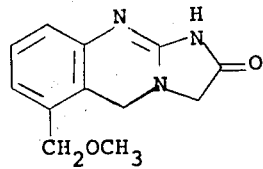

To a solution of 12.0 g (48 mmole) of N-[2-(α-methoxymethyl)-6-aminobenzyl]glycine ethyl ether (11a) in 200 ml of 95% ethyl alcohol was added at room temperature a solution of 5.0 g (48 mmole) of cyanogen bromide in 50 ml of 95% ethyl alcohol. The mixture was allowed to stir at room temperature for 15 mins., heated to reflux for 17 hrs., cooled to room temperature and the solvent removed in vacuo. To the resulting semisolid mass was added 100 ml of water and enough 10% hydrochloric acid to effect dissolution. The acidic solution was washed with ether, made basic (pH~8) by dropwise addition of concentrated ammonium hydroxide and allowed to stir at room temperature for 0.5 hrs. The precipitate was filtered under suction, washed with water and dried yielding 7.9 g (72% yield) of a colorless powder identified as the title product. Purification was effected by crystallization from nitromethane (mp >225) or hydrochloride salt formation from isopropanol (mp 238°–40° w/decomp).

Anal. calc'd. for $C_{12}H_{13}N_3O_2$: C, 62.33; H, 5.67; N, 18.16. Found: C, 62.01; H, 5.76; N, 18.30. Calc'd. for $C_{12}H_{13}N_3O_2 \cdot HCl \cdot \frac{1}{2} H_2O$: C, 52.09; H, 5.46; N, 15.17. Found: C, 52.28; H, 5.48; N, 15.07.

EXAMPLE 9

Preparation of Ethyl β-(2-methoxymethyl-6-nitrobenzylamino)-propionate (10b).

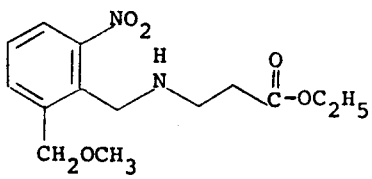

Substitution in the procedure of example 6 for the glycine ethyl ester hydrochloride used therein of an equimolar quantity of ethyl 3-amino-propionate produces the title compound 10b.

EXAMPLE 10

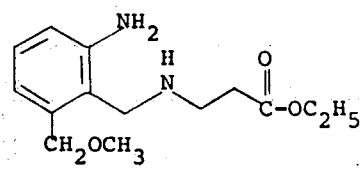

Preparation of Ethyl β-(2-methoxymethyl)-6aminobenzylamino)-propionate (11b).

Substitution in the procedure of example 7 for the compound 10a used therein of an equimolar quantity of compound 10b produces the title compound 11b.

EXAMPLE 11

Preparation of 7-Methoxymethyl 6-[H]-1,2,3,4-tetrahydropyrimido[2,1-b]-quinazolin-2-one (12b).

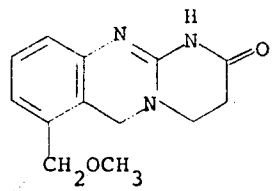

Substitution in the procedure of example 8 for the compound 11a used therein of an equimolar amount of 11b produces the title compound 12 b.

Example 12

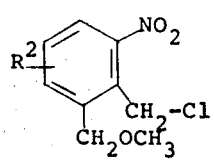

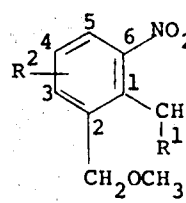

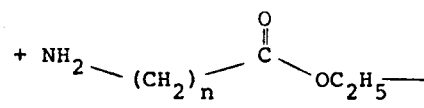

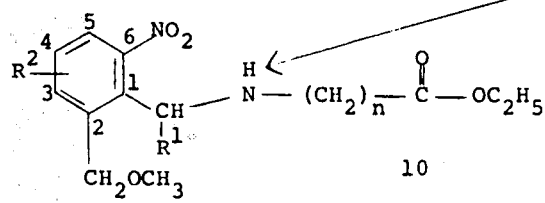

Preparation of Substituted N-(o-Nitrobenzyl)-Ethyl Glycinates and Aminopropionates.

Substitution in the procedure of example 6 for the 2-(α-methoxymethyl)-6-nitrobenzyl chloride used therein of an equimolar quantity of the appropriately $R^1$ and $R^2$-substituted o-nitrobenzylchloride produced the compounds having formula 10 in which n, $R^1$ and $R^2$ are as designated:

| Compound No. | $R^1$ | $R^2$ | n |
|---|---|---|---|
| 10c | H | 3-Cl | 1 |
| 10d | H | 4-Cl | 1 |
| 10e | H | 3-F | 1 |
| 10f | H | 3-$CH_3$ | 1 |
| 10g | H | 4-$OCH_3$ | 1 |
| 10h | H | 5-$OCH_3$ | 1 |
| 10i | H | 3-$OCH_3$ | 1 |
| 10j | H | 3-Cl | 2 |
| 10k | H | 3-$CH_3$ | 2 |
| 10L | H | 4-$CH_3$ | 2 |
| 10m | H | 5-$CH_3$ | 2 |
| 10n | H | 5-$OCH_3$ | 2 |
| 10o | H | 4-$OCH_3$ | 2 |
| 10p | $CH_3$ | H | 1 |
| 10q | $CH_3$ | H | 2 |
| 10r | H | 4-$CH_3$ | 1 |
| 10s | H | 3-Br | 1 |
| 10t | H | 5-F | 1 |

Example 13

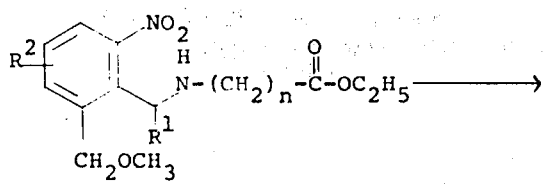

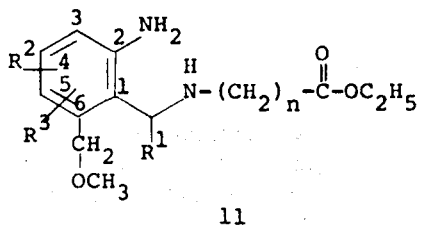

Example 14

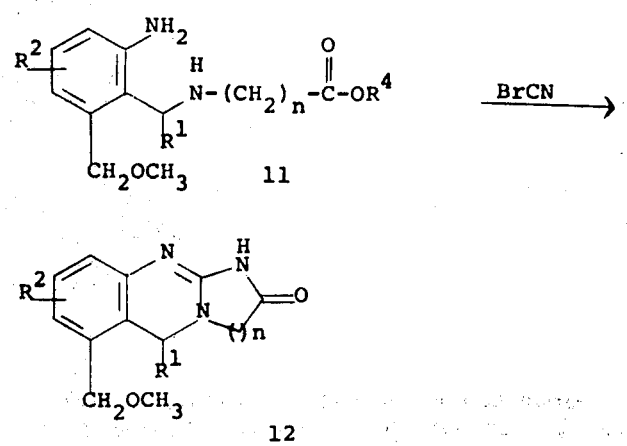

Substitution in the procedure of example 7 for the N-[2-(α-methoxymethyl)-6-nitrobenzyl]glycine ethyl ester used therein of an equimolar quantity of the appropriately $R^1$ and $R^2$ substituted compound 10 produced the compounds having the formula 11:

Substitution in the procedure of example 8 for the N-[2-(α-methoxymethyl)-6-aminobenzyl]-glycine ethyl ester therein of an equimolar quantity of the appropriate compound 11 described in example 7 produces the compound 12 listed below:

| Compound No. | n | $R^1$ | $R^2$ |
|---|---|---|---|
| 11c | 1 | H | 3-Cl |
| 11d | 1 | H | 4-Cl |
| 11e | 1 | H | 3-F |
| 11f | 1 | H | 3-CH₃ |
| 11g | 1 | H | 4-OCH₃ |
| 11h | 1 | H | 5-OCH₃ |
| 11i | 1 | H | 3-OCH₃ |
| 11j | 2 | H | 3-Cl |
| 11k | 2 | H | 3-CH₃ |
| 11L | 2 | H | 4-CH₃ |
| 11m | 2 | H | 5-CH₃ |
| 11n | 2 | H | 5-OCH₃ |
| 11o | 2 | H | 4-OCH₃ |
| 11p | 1 | CH₃ | H |
| 11q | 2 | CH₃ | H |
| 11r | 1 | H | 4-CH₃ |
| 11s | 1 | H | 3-Br |
| 11t | 1 | H | 5-F |

| Compound No. | n | $R^1$ | $R^2$ |
|---|---|---|---|
| 12c | 1 | H | 7-Cl |
| 12d | 1 | H | 8-Cl |
| 12e | 1 | H | 7-F |
| 12f | 1 | H | 7-CH₃ |
| 12g | 1 | H | 8-OCH₃ |
| 12h | 1 | H | 9-OCH₃ |
| 12i | 1 | H | 7-OCH₃ |
| 12j | 2 | H | 7-Cl |
| 12k | 2 | H | 7-CH₃ |
| 12L | 2 | H | 8-CH₃ |
| 12m | 2 | H | 10-OCH₃ |
| 12n | 2 | H | 10-OCH₃ |
| 12p | 1 | CH₃ | H |
| 12q | 2 | CH₃ | H |
| 12r | 1 | H | 8-CH₃ |
| 12s | 1 | H | 6-Br |
| 12t | 1 | H | 5-F |

EXAMPLE 15

Alternate preparation of Ethyl 3-(2-methoxymethyl-6-nitrobenzylamino)-propionate (10b) hydrochloride.

2-Methoxymethyl-6-nitrobenzylamine hydrochloride (20.4 g., 0.114 mole) is dissolved in a minimum volume of water and the solution is made strongly basic by the addition of 10% sodium hydroxide. The clear oil which forms is extracted into two 120-ml. portions of ether. The ether is dried with 10 g. of anhydrous sodium sulfate, filtered, and finally dried over Drierite. The dried solution is filtered and evaporated, leaving a yellow oil. The oil is dissolved in 100 ml. of absolute ethanol and 11.4 g (0.114 mole) of freshly distilled ethyl acrylate is added. This solution is allowed to stand overnight and the solvent removed by distillation from a steamcone. The oily residue is dissolved in 200 ml. of dry ether, the solution is cooled in an ice bath, and treated with dry hydrogen chloride. When precipitation is complete, the solid is filtered and dissolved in 120 ml. of boiling absolute ethanol. The hydrochloride crystallizes from this solution on cooling yielding the title product. By concentrating and cooling the mother liquor, additional title product g. is obtained.

Example 16

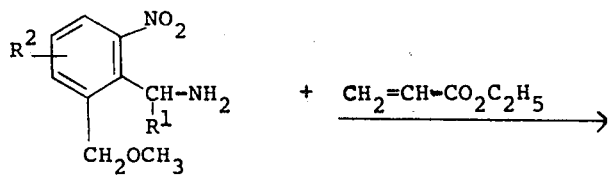

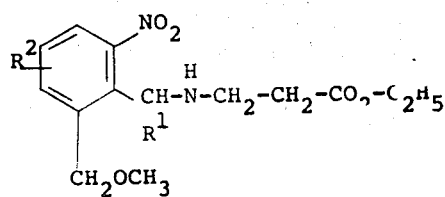

Substitution in the procedure of example 15 for the o-nitrobenzylamine used therein of an equimolar quantity of appropriately $R^1$ and $R^2$ substituted 2-methoxymethyl-1-nitrobenzylamine produces compounds 10 in which $R^1$ and $R^2$ are as defined in the specification.

EXAMPLE 17

Preparation of 7-Bromo-6-methoxymethyl-1,2,3,5-tetrahydroimidazo[2,1-b]-quinazolin-2-one.

To a vigorously stirred solution of 1.87 g. (0.01 mole) of 6-methoxymethyl-1,2,3,5-tetrahydroimidazo[2,1-b]-quinazolin-2-one in 40 ml. of glacial acetic acid is added dropwise at room temperature 1.60 g. (0.01 mole) of bromine. The mixture is stirred at room temperature for one hour, water (50 ml.) is added and the volume concentrated (10–15 ml.) in vacuo. Additional water (50 ml.) is added, the solution made basic with ammonium hydroxice, warmed and the insoluble material filtered under suction. The colorless solid is washed with water, dried and crystallized from 50 ml. of 5% hydrochloric acid yielding the title product as a colorless solid. Purification is effected by crystallization from methanol/ether to yield the title product.

EXAMPLE 18

Preparation of 7-Nitro-6-methoxymethyl-1,2,3,5-tetrahydroimidazo[2,1-b]-quinazolin-2-one.

To a stirred, 0° suspension of 11.20 g. (6.0 × 10–2 moles) of 6-methoxymethyl-1,2,3,5-tetrahydroimidazo[2,1-b]-quinazolin-2-one in acetonitrile (150 ml.) is added dropwise 83.0 g. (6.6 × 10$^{12}$ moles of nitric acid) of a 5% nitric acid/sulfuric acid solution. The mixture is allowed to stir at 0° for 45 minutes, warmed to room temperature and stirred an additional two hours. The mixture is poured into 700 ml. of ice water, the organic layer separated, the acidic aqueous solution washed with methylene chloride (2 × 100 ml.) and filtered. The aqueous solution is made basic (pH 8) by the dropwise addition of 40% sodium hydroxide, the basic solution stirred for 30 minutes and the precipitate filtered under suction. The yellow solid is washed with water, then acetone and dried under high vacuum. The solid is suspended in water (350 ml.), the solution saturated with hydrogen chloride, heated to boiling and filtered. Saturated sodium chloride solution (100 ml.) is added, the mixture cooled and the precipitate isolated yielding the title product as a yellow powder.

EXAMPLE 19

Preparation of 7-Amino-6-methoxymethyl-1,2,3,5-tetrahydroimidazo-[2,1-b]-quinazolin-2-one.

To a suspension of 9.18 g. (3.4 × 10$^{-2}$ mole) of 7-Nitro-6-methoxymethyl-1,2,3,5-tetrahydroimidazo[2,1-b]-quinazolin-2-one hydrochloride in 95% ethanol (300 ml.) is added 10 ml. of concentrated hydrochloric acid and 0.45 g. of 10% Pd/C catalyst. The mixture is placed on a Paar hydrogenator, shaken until theoretical hydrogen is absorbed, removed and water (150 ml.) added to effect dissolution of the precipitate. The mixture is filtered under suction, the catalyst washed with 95% ethanol and the mixture evaporated to dryness yielding the title product as a yellow powder.

EXAMPLE 20

Preparation of 7-Hydroxy-6-methoxymethyl-1,2,3,5-tetrahydroimidazo-[2,1-b]-quinazolin-2-one hydrochloride.

A mixture of 16.0 g. (6.91 × 10⁻² moles) of compound 121 and 750 ml. of 48% aqueous hydrobromic acid is heated to reflux for 22 hours, the mixture cooled by the addition of ice, the precipitate filtered under suction, washed with water and dried. The precipitate is dissolved in a minimum amount of 1N hydrochloric acid, treated with charcoal, filtered and cooled (4°) overnight. The precipitate is isolated and dried yielding the title product as less needles.

EXAMPLE 21

Preparation of 8-Bromo-6-methoxymethyl-6-[H]-1,2,3,4-tetrahydropyrimido[2,1-b]quinazolin-2-one.

Substitution in the procedure of example 17 for the 6-methoxymethyl-1,2,3,5-tetrahydroimidazo[2,1-b]-quinazolin-2-one used therein of an equimolar quantity of 6-methoxymethyl-6-[H]-1,2,3,4-Tetrahydropyrimido[2,1-b]quinazolin-2-one at about 60° C. produces the title compound. We claim:

1. A compound having the formula

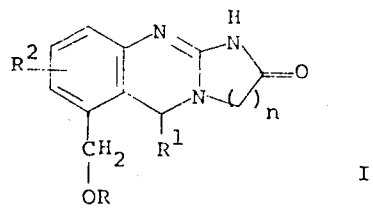

I in which $R^1$ is H, phenyl or (lower)alkyl, R is (lower)alkyl, $R^2$ is hydrogen, chloro, bromo, fluoro, $CF_3$, hydroxy, (lower)alkyl of 1 to 3 carbon atoms or (lower)alkoxy of 1 to 3 carbon atoms and $n$ is an integer of 1 or 2; or a pharmaceutically acceptable acid addition salt thereof.

2. A compound of claim 1 having the formula

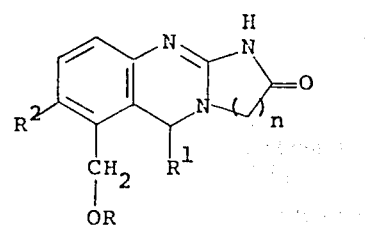

I in which $R^1$ is H, phenyl or (lower)alkyl, R is (lower)alkyl, $R^2$ is hydrogen, chloro, bromo, fluoro, $CF_3$, hydroxy, (lower)alkyl of 1 to 3 carbon atoms or (lower)alkoxy of 1 to 3 carbon atoms and $n$ is an integer of 1 or 2; or a pharmaceutically acceptable acid addition salt thereof.

3. A compound of claim 2 having the formula

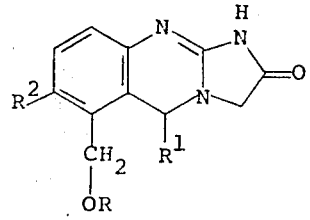

in which $R^1$ is H, phenyl or (lower)alkyl, R is (lower)alkyl, $R^2$ is hydrogen, chloro, bromo, $CF_3$, fluoro, hydroxy, (lower)alkyl of 1 to 3 carbon atoms or (lower)alkoxy of 1 to 3 carbon atoms, or a pharmaceutically acceptable acid addition salt thereof.

4. A compound of claim 2 having the formula in which R is (lower)alkyl, $R^2$ is hydrogen, chloro, bromo, fluoro, $CF_3$, hydroxy, (lower)alkoxy of 1 to 3 carbon atoms or (lower)alkyl of 1 to 3 carbon atoms; or a pharmaceutically acceptable acid addition salt thereof.

5. A compound of claim 2 having the formula in which R is (lower)alkyl of 1 to 3 carbon atoms, $R^2$ is H, hydroxy, (lower)alkoxy of 1 to 3 carbon atoms or (lower)alkyl of 1 to 3 carbon atoms, chloro, or fluoro; or a pharmaceutically acceptable acid addition salt thereof.

6. A compound of claim 2 having the formula

29

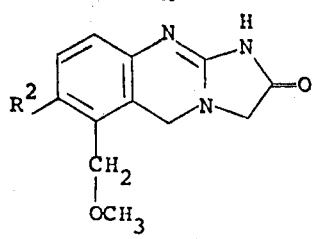

in which R² is H, Cl, methoxy, methyl or hydroxy; or the hydrochloride salt thereof.

7. The compound of claim 6 in which R² is methoxy; or the hydrochloride salt thereof.

8. The compound of claim 6 in which R² is methyl; or the hydrochloride salt thereof.

9. The compound having the formula

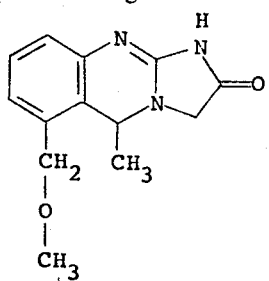

or a pharmaceutically acceptable acid addition salt thereof.

10. The hydrochloride salt of the compound of claim 9.

11. The compound having the formula

30

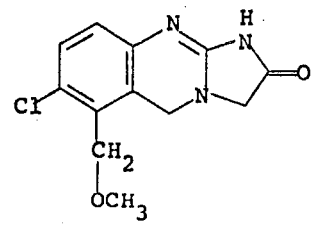

or a pharmaceutically acceptable acid addition salt thereof.

12. The hydrochloride salt of the compound of claim 11.

13. The compound having the formula

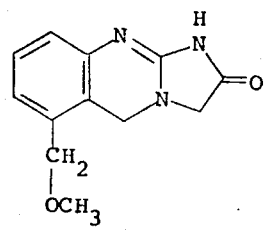

or a pharmaceutically acceptable acid addition salt thereof.

14. The hydrochloride salt of the compound of claim 13.

* * * * *